(12) United States Patent
Takaichi et al.

(10) Patent No.: US 11,578,142 B2
(45) Date of Patent: Feb. 14, 2023

(54) ACID TYPE CARBOXYLATED CELLULOSE NANOFIBER

(71) Applicant: NIPPON PAPER INDUSTRIES CO., LTD., Kita-ku (JP)

(72) Inventors: Satoshi Takaichi, Tokyo (JP); Takeshi Nakatani, Tokyo (JP); Masahiro Morita, Tokyo (JP); Shinichi Onogi, Tokyo (JP); Takeshi Fujii, Tokyo (JP); Kenichiro Sasaki, Tokyo (JP); Makoto Matsumoto, Tokyo (JP); Takeshi Nakayama, Tokyo (JP)

(73) Assignee: NIPPON PAPER INDUSTRIES CO., LTD., Kita-ku (JP)

( * ) Notice: Subject to any disclaimer, the term of this patent is extended or adjusted under 35 U.S.C. 154(b) by 819 days.

(21) Appl. No.: 16/471,798

(22) PCT Filed: Nov. 2, 2017

(86) PCT No.: PCT/JP2017/039814
§ 371 (c)(1),
(2) Date: Jun. 20, 2019

(87) PCT Pub. No.: WO2018/116661
PCT Pub. Date: Jun. 28, 2018

(65) Prior Publication Data
US 2020/0087417 A1  Mar. 19, 2020

(30) Foreign Application Priority Data

Dec. 21, 2016 (JP) .............................. JP2016-248433
Feb. 8, 2017 (JP) .............................. JP2017-021487
Apr. 10, 2017 (JP) .............................. JP2017-077624
May 22, 2017 (JP) .............................. JP2017-100851
Oct. 17, 2017 (JP) .............................. JP2017-201128

(51) Int. Cl.
*C08B 15/04* (2006.01)
*C08L 1/04* (2006.01)
*D01F 2/28* (2006.01)

(52) U.S. Cl.
CPC .............. *C08B 15/04* (2013.01); *C08L 1/04* (2013.01); *D01F 2/28* (2013.01); *C08L 2205/16* (2013.01)

(58) Field of Classification Search
CPC ............. C08B 15/04; D01F 2/28; C08L 1/04; C08L 2205/16
See application file for complete search history.

(56) References Cited

U.S. PATENT DOCUMENTS

| 2010/0316863 | A1 | 12/2010 | Kumamoto et al. |
| 2012/0283363 | A1 | 11/2012 | Kumamoto et al. |
| 2014/0053828 | A1 | 2/2014 | Tsuji et al. |
| 2014/0356767 | A1 | 12/2014 | Kimura et al. |
| 2015/0027648 | A1 | 1/2015 | Tsuji et al. |
| 2015/0267070 | A1 | 9/2015 | Tsuji et al. |
| 2016/0200964 | A1 | 7/2016 | Goi et al. |
| 2018/0016402 | A1 | 1/2018 | Miyazaki et al. |
| 2018/0066072 | A1 | 3/2018 | Takaichi et al. |
| 2018/0118991 | A1 | 5/2018 | Yoshida et al. |
| 2018/0131005 | A1 | 5/2018 | Kimura et al. |

FOREIGN PATENT DOCUMENTS

| JP | 2004-59618 A | 2/2004 |
| JP | 2005-23281 A | 1/2005 |
| JP | 2006-124598 A | 5/2006 |
| JP | 2006-282926 A | 10/2006 |
| JP | 2009-57552 A | 3/2009 |
| JP | 2009-197122 A | 9/2009 |
| JP | 2010-37200 A | 2/2010 |
| JP | 2011-140632 A | 7/2011 |
| JP | 2012-1626 A | 1/2012 |
| JP | 2012-122077 A | 6/2012 |
| JP | 2012-207133 A | 10/2012 |
| JP | 2012-207135 A | 10/2012 |
| JP | 2012-214717 A | 11/2012 |
| JP | 2013-14741 A | 1/2013 |
| JP | 2013-18918 A | 1/2013 |
| JP | WO 2013/047218 A1 | 4/2013 |
| JP | WO 2013/121781 A1 | 8/2013 |
| JP | WO 2014/061485 A1 | 4/2014 |
| JP | 2014-105233 A | 6/2014 |
| JP | 2014-114338 A | 6/2014 |
| JP | 2014-125607 A | 7/2014 |
| JP | WO 2015/029960 A1 | 3/2015 |

(Continued)

OTHER PUBLICATIONS

Extended European Search Report dated Jul. 22, 2020 in European Patent Application No. 17882768.9, 6 pages.
Isogai A., et al., "TEMPO-oxidized cellulose nanofibers", Nanoscale, vol. 3, No. 1, Jan. 1, 2011, XP055184316, pp. 71-85.
International Search Report dated Nov. 28, 2017 in PCT/JP2017/039814 filed on Nov. 2, 2017.
Japanese Office Action dated Jan. 12, 2021 in Japanese Patent Application No. 2016-248433 (with English translation).
Yui, Y., et al., "Functionalization of Cotton Fabrics by Tempo-Mediated Oxidation", Sen'I Gakkaishi, vol. 69, No. 11, 2013, pp. 222-228 (with English abstract).

*Primary Examiner* — Leigh C Maier
*Assistant Examiner* — Everett White
(74) *Attorney, Agent, or Firm* — Oblon, McClelland, Maier & Neustadt, L.L.P.

(57) ABSTRACT

The present invention intends to provide an acid type carboxylated cellulose nanofiber having a high viscosity in a low shear region, or to provide an acid type carboxylated cellulose nanofiber having a very short fiber length, and the acid type carboxylated cellulose nanofiber has a carboxy group at least in part of a constituent unit constituting a cellulose molecular chain, wherein a viscosity of water dispersion with a content from 0.95 to 1.05% by mass is 400 Pa·s or higher at a shear velocity from 0.003 to 0.01 s$^{-1}$ at 30° C., or an average fiber length is from 50 to 500 nm and a ratio of fibers having a fiber length of 300 nm or shorter is 50% or higher.

7 Claims, 1 Drawing Sheet

(56) References Cited

FOREIGN PATENT DOCUMENTS

| | | |
|---|---|---|
| JP | 2015-221845 A | 12/2015 |
| JP | 2016-52620 A | 4/2016 |
| JP | 5939695 B1 | 6/2016 |
| JP | 5944564 B1 | 7/2016 |
| JP | 5996082 B1 | 9/2016 |
| JP | WO 2016/136453 A1 | 9/2016 |
| JP | 2016-183329 A | 10/2016 |
| JP | 2016-211116 A | 12/2016 |
| JP | WO 2017/141800 A1 | 8/2017 |
| JP | 6229090 B1 | 11/2017 |
| JP | 2018-9116 A | 1/2018 |
| WO | WO 2013/137140 A1 | 9/2013 |
| WO | WO 2016/186055 A1 | 11/2016 |

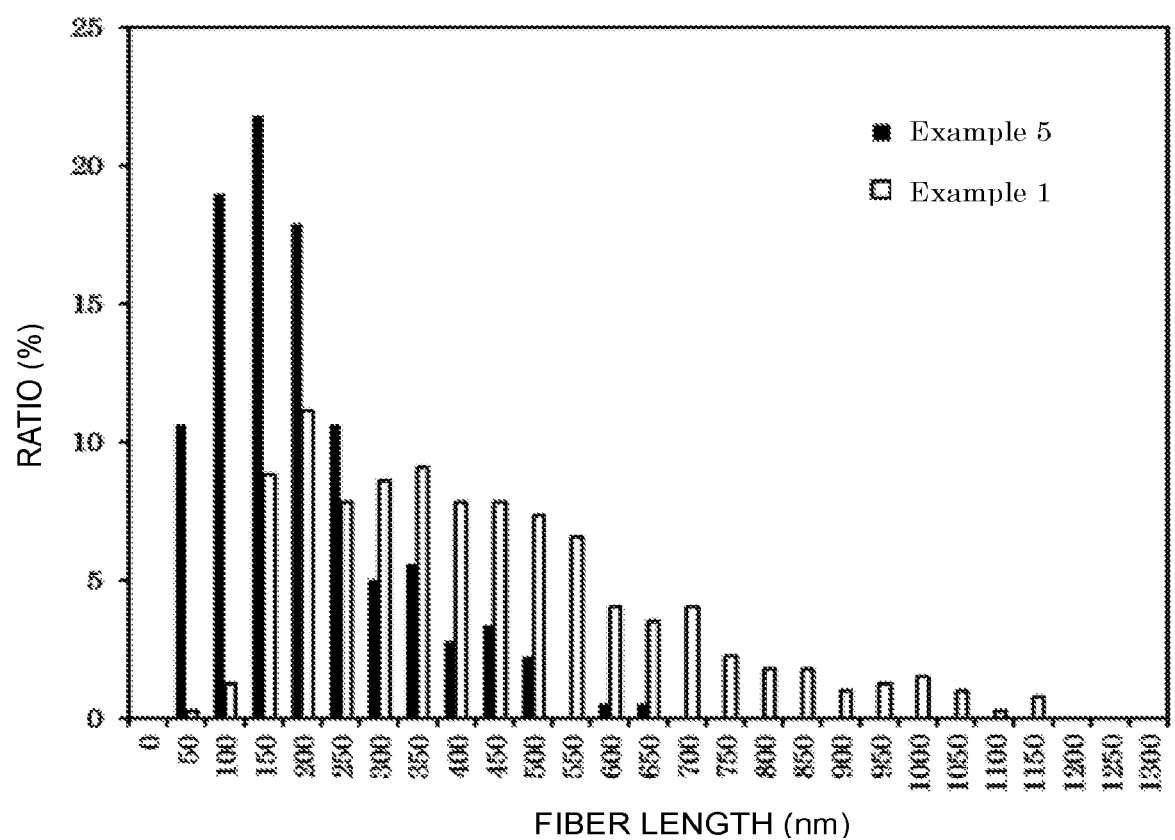

ACID TYPE CARBOXYLATED CELLULOSE NANOFIBER

TECHNICAL FIELD

The present invention relates to an acid type carboxylated cellulose nanofiber.

BACKGROUND ART

When a cellulose raw material is treated in the copresence of 2,2,6,6-tetramethyl-1-piperidine-N-oxy radical (thereinafter, this is also called "TEMPO") and sodium hypochlorite being a cheap oxidant, the carboxy groups can be efficiently introduced onto the surface of the cellulose microfibril. When the cellulose to which the carboxy groups are introduced is processed in water by using a mixer or the like, highly viscous and transparent water dispersion of the cellulose nanofiber can be obtained.

Since the carboxy groups are introduced onto the surface of the cellulose nanofiber as described above, the reforming can be freely performed at these carboxy groups taking as starting points. In addition, since the cellulose nanofiber is in the form of dispersion liquid, the reforming can be also performed by blending it with a water-soluble polymer or by compounding it with an organic or an inorganic pigment. Furthermore, the cellulose nanofiber can be formed to a sheet or a fiber. Because of these characteristics, the development of the novel high-functional goods such as a high-functional packaging material, a transparent organic substrate member, a high-functional fiber, a separation membrane, and a regenerative medicinal material has been studied by applying the cellulose nanofiber thereto.

As one example of the novel high-functional goods, Patent document 1 disclosed a spray composition including the carboxylated cellulose fiber and water. Since the manufacturing process thereof does not involve a desalting process, the carboxylated cellulose fiber included in the spray composition described in the Patent document 1 is presumed to be sodium type salt in view of the manufacturing process.

With an aim to reduce an energy required for fibrillating the cellulose to which the carboxy groups are introduced, it was proposed to carry out an alkali hydrolysis treatment before the fibrillation treatment (see, for example, Patent document 2). Furthermore, with an aim to further reduce energy required for the fibrillation, in addition to the alkali hydrolysis treatment before the fibrillation treatment, it was proposed to carry out a viscosity lowering process (see, for example, Patent document 3).

PRIOR ART DOCUMENTS

Patent Documents

Patent Document 1: JP-A-2010-37200
Patent Document 2: WO-A-2013/137140
Patent Document 3: JP-A-2012-214717

SUMMARY OF INVENTION

Problem to be Solved by the Invention

In the Patent document 1, it is described that there is an additive whose functionality is decreased in the presence of a salt. Therefore, when the carboxylated cellulose fiber is used in a spray composition, the carboxylated cellulose fiber being converted to acid type by a desalting treatment is preferable.

However, the acid type carboxylated cellulose nanofiber obtained by an acid treatment of the carboxylated cellulose fiber with the mineral acid such as hydrochloric acid has been prone to be low in the viscosity in the low shear velocity region (hereinafter, this is also called "low shear region"). Therefore, when they are used in the spray composition, there has been a case that a thickener was added therein for avoiding the dripping.

Accordingly, the development of the acid type carboxylated cellulose nanofiber having a high viscosity in the low shear region has been desired.

In the methods proposed in the Patent documents 2 and 3, when the cellulose to which the carboxy groups are introduced is alkali-hydrolyzed before fibrillation, the obtained carboxylated cellulose nanofiber is the alkali metal salt. When the resultant was subjected to a desalting treatment by acids, the acid type carboxylated cellulose nanofiber could not be isolated.

The inventors of the present invention studied the reason why the acid type carboxylated cellulose nanofiber could not be isolated. And then, they found that when the carboxylated cellulose nanofiber is produced by fibrillation after the alkali hydrolysis, the ratio of the nanofibers having a very short fiber length was increased. Therefore, when the filtration was carried out after the desalting treatment by the acid treatment, it was found that these could not be isolated as the residue, but these were included in the filtrates together with NaCl and the like.

Among novel high functional goods, since there is a field in which the acid type carboxylated cellulose nanofiber having a very short fiber length is wanted, it is desirable to isolate and provide these fibers.

A first object of the present invention is to provide an acid type carboxylated cellulose nanofiber having a high viscosity in the low shear region.

A second object of the present invention is to provide an acid type carboxylated cellulose nanofiber having a very short fiber length.

Means for Solving Problem

The inventors of the present invention carried out extensive investigations about the first object, and as the results, it was found that the acid type carboxylated cellulosed nanofiber obtained by a desalting treatment with cation exchange resins could solve the first object, and the present invention could be completed.

Furthermore, the inventors of the present invention carried out extensive investigations about the second object, and as the results, it was found that the oxidized cellulose to which carboxy groups are introduced is alkali-hydrolyzed, and thereafter the carboxylated cellulose nanofiber salt obtained by fibrillation of the cellulose was subjected to a desalting treatment with cation exchange resins, the second object could be solved, and the present invention could be completed.

That is, the present inventors provide the following [1] to [8]:

[1] An acid type carboxylated cellulose nanofiber (hereinafter, also referred to as "nanofiber A"), comprising a carboxy group at least in part of a constituent unit constituting a cellulose molecular chain, wherein a viscosity of water dispersion with a content from 0.95% to 1.05% by mass is 400 Pa·s or higher at a shear velocity from 0.003 to 0.01 s$^{-1}$ at 30° C.

[2] An acid type carboxylated cellulose nanofiber (hereinafter, also referred to as "nanofiber B"), comprising a carboxy group at least in part of a constituent unit constituting a cellulose molecular chain, wherein an average fiber length is from 50 to 500 nm, and a ratio of fibers having a fiber length of 300 nm or shorter is 50% or higher.

[3] The acid type carboxylated cellulose nanofiber according to [2], wherein an average fiber diameter is from 2 to 50 nm.

[4] The acid type carboxylated cellulose nanofiber according to [2], wherein an average fiber diameter is from 2 to 30 nm.

[5] The acid type carboxylated cellulose nanofiber according to any one of [2] to [4], wherein a ratio of fibers having a fiber length of 600 nm or longer is lower than 20%.

[6] The acid type carboxylated cellulose nanofiber according to any one of [1] to [5], wherein at least part of the cellulose molecular chain is composed of a constituent unit having a carboxy group formed by selectively oxidizing a carbon atom having a primary hydroxy group at a C6 position of a glucopyranose unit.

[7] The acid type carboxylated cellulose nanofiber according to any one of [1] to [6], wherein an amount of the carboxy group relative to a bone dry mass of the carboxylated cellulose nanofiber is from 0.6 to 2.0 mmol/g.

[8] The acid type carboxylated cellulose nanofiber according to any one of [1] to [6], wherein an amount of the carboxy group relative to a bone dry mass of the carboxylated cellulose nanofiber is from 0.8 to 2.0 mmol/g.

Effect of the Invention

According to the present invention, the acid type carboxylated cellulose nanofiber having a high viscosity in a low shear region can be provided.

In addition, according to the present invention, the acid type carboxylated cellulose nanofiber having a very short fiber length can be provided.

BRIEF DESCRIPTION OF DRAWING

FIG. 1 is a graph illustrating the fiber length distributions of the acid type carboxylated cellulose nanofibers corresponding to Examples 1 and 5.

EMBODIMENTS FOR CARRYING OUT THE INVENTION

Hereinafter, the present invention will be explained in detail in accordance with preferable embodiments thereof. Note that in this specification, "acid type carboxylated cellulose nanofiber" means the carboxylated cellulose nanofiber that is subjected the metal salt such as a sodium salt to a desalting treatment so that the salt thereof is converted to the acid type.

[1. Nanofiber A]

The nanofiber A of the present invention is the acid type carboxylated cellulose nanofiber. The nanofiber A of the present invention has the carboxy groups at least in part of the constituent unit constituting the cellulose molecular chain, and a viscosity of the water dispersion thereof with the content from 0.95% to 1.05% by mass is 400 Pa·s or higher at a shear velocity from 0.003 to 0.01 s$^{-1}$ at 30° C.

Accordingly, when the nanofiber A of the present invention is used, for example, in a spray composition, it is possible to avoid the dripping even without using other thickener or with a small use amount of other thickener even if used.

In the nanofiber A of the present invention, a lower limit value of the viscosity of the water dispersion with the content from 0.95 to 1.05% by mass is 400 Pa·s or higher, preferably 500 Pa·s or higher, more preferably higher than 925 Pa-s, further preferably 930 Pa-s or higher, and further more preferably 950 Pa·s or higher, at the shear velocity from 0.003 to 0.01 s$^{-1}$ at 30° C. The upper limit value thereof is preferably 100,000 Pa·s or lower, more preferably 50,000 Pa·s or lower, and further preferably 25,000 Pa·s or lower.

The viscosity thereof can be measured, for example, by preparing the water dispersion having the concentration from 0.95 to 1.05% by mass by adding water to the nanofiber A, and then measuring the viscosity thereof by using a viscoelastic rheometer (for example, "MCR 301" manufactured by Anton Paar GmbH) at a prescribed shear velocity.

The average fiber length of the nanofiber A of the present invention is preferably from 200 to 2,000 nm, more preferably from 250 to 1,500 nm, further preferably from 300 to 1,000 nm, and further more preferably from 550 to 1,000 nm.

In addition, the average fiber diameter of the nanofiber A of the present invention is preferably from 1.50 to 1,000 nm, more preferably from 2.00 to 750 nm, further preferably from 2.50 to 500 nm, and further more preferably from 2.85 to 500 nm.

[2. Nanofiber B]

The nanofiber B of the present invention is the acid type carboxylated cellulose nanofiber. The nanofiber B of the present invention has the carboxy groups at least in part of the constituent unit constituting the cellulose molecular chain, and an average fiber length thereof is from 50 to 500 nm, and a ratio of fibers having the fiber length of 300 nm or shorter is 50% or higher.

When the oxidized cellulose is treated with the alkali hydrolysis followed by a desalting treatment thereof with cation exchange resins, the nanofiber B satisfying the two features relating to the fiber length described above can be obtained by isolation.

In the nanofiber B of the present invention, the average fiber length is from 50 to 500 nm, and preferably from 100 to 400 nm. In addition, the ratio of fibers having the fiber length of 300 nm or shorter is 50% or higher, and preferably 60% or higher. Furthermore, the ratio of fibers having the fiber length of 600 nm or longer is preferably less than 20%, more preferably less than 15%, and further preferably less than 10%. In the nanofiber B satisfying such the conditions, the fiber length distribution is converged into the short region. Accordingly, it can be especially expected for the application as a composite material with a resin or with a rubber, or as an additive to a paint material.

In the nanofiber B of the present invention, the average fiber diameter is preferably from 2.0 to 50 nm, from 2.0 to 40 nm, and from 2.0 to 30 nm, more preferably from 2.5 to 30 nm, from 3.0 to 30 nm, and from 3.0 to 20 nm, and further preferably from 3.0 to 15 nm.

The average fiber length of the carboxylated cellulose nanofiber can be calculated in the manner as described below. The carboxylated cellulose nanofiber is fixed onto a mica cut peace, and the lengths of 200 fibers are measured by using an atomic force microscope (AFM) to calculate the length (weight) average fiber length. Here, the measurement of the fiber length is carried out in an arbitrary length region by using an image analysis software WinROOF (manufactured by Mitani Corp.). The ratio of fibers having the fiber length of 300 nm or shorter or of 600 nm or longer can be calculated as the ratio of the carboxylated cellulose nanofibers having the fiber length of 300 nm or shorter or of 600 nm or longer, relative to the total measured fibers.

The average fiber diameter of the carboxylated cellulose nanofiber can be calculated in the manner as described below. The carboxylated cellulose nanofiber water dispersion is prepared by diluting the carboxylated cellulose nanofiber so as to bring the concentration thereof to 0.001% by mass. This diluted dispersion is thinly spread on a mica-made sample plate, and then, the resultant is dried by heating at 50° C. to prepare the observation sample. The section height of the shape image observed with an atomic force microscope (AFM) is measured to calculate the weighted average fiber diameter.

In the nanofiber A and the nanofiber B of the present invention, at least part of the cellulose molecular chain is preferably composed of the constituent units having the carboxy groups formed by selectively oxidizing the carbon atom having a primary hydroxy group at C6 position of the glucopyranose unit. Here, the cellulose molecular chain may be composed of only the constituent units having the carboxy groups formed by selectively oxidizing the carbon atom having a primary hydroxy group at C6 position of the glucopyranose unit.

Here, the glucopyranose unit is a constituent unit represented by the following formula (0).

[Chem. 1]

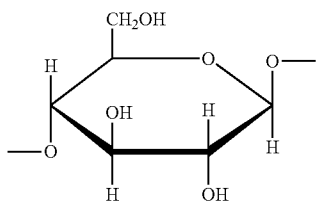

(0)

In the nanofiber A and the nanofiber B of the present invention, the amount of the carboxy groups relative to the bone dry mass of the carboxylated cellulose nanofiber is preferably from 0.6 to 2.0 mmol/g, more preferably from 0.8 to 2.0 mmol/g, further preferably from 1.2 to 2.0 mmol/g, and further more preferably from 1.4 to 1.8 mmol/g. When the amount of the carboxy groups is 0.6 mmol/g or larger, the carboxy groups are introduced onto the surface of the cellulose molecular chain to give an electrostatic repulsion action thereto. Accordingly, the nanofiber can be produced by fibrillation. When the amount of the carboxy groups is 0.8 mmol/g or larger, the carboxy groups are sufficiently introduced onto the surface of the cellulose molecular chain to give an electrostatic repulsion thereto. Accordingly, the nanofibers can be readily produced by fibrillation.

The amount of the carboxy groups can be measured in the manner as described below. 60 mL of the slurry of the carboxylated cellulose (water dispersion) with the concentration of 0.5% by mass is prepared. 0.1 M hydrochloric acid aqueous solution is added to the prepared slurry to adjust the pH at 2.5, and thereafter 0.05 N sodium hydroxide aqueous solution is added dropwise thereto till pH 11 while measuring an electric conductivity. From the sodium hydroxide amount (a) consumed in the weakly acidic neutralization stage in which the change of the electric conductivity is moderate, the amount of the carboxy groups can be calculated by using the following equation:

Amount of carboxy groups [mmol/g carboxylated celluloses]=a [mL]×0.05/mass of carboxylated cellulose [g]

Usually, the amount of the carboxy groups in the carboxylated cellulose nanofiber is the same as the amount of the carboxy groups in the carboxylated cellulose.

[3. Production Method]

The carboxylated cellulose nanofiber may be produced, for example, in the manner described below. The cellulose raw material is oxidized to prepare an oxidized cellulose (hereinafter, this process is also called "oxidation treatment"), the prepared oxidized cellulose is fibrillated (hereinafter, this process is also called "fibrillation treatment"), and then the fibrillated oxidized cellulose is subjected to a desalting treatment with cation exchange resins (hereinafter, this process is also called "desalting treatment") to produce the nanofiber A. By using the oxidized cellulose which is subjected to the alkali hydrolyzed (hereinafter, this process is also called "alkali hydrolysis treatment") after the oxidation treatment and before the fibrillation treatment, the nanofiber B can be produced.

Alternatively, the acid type carboxylated cellulose nanofiber may be produced in such a manner that the prepared oxidized cellulose or the hydrolyzed oxidized cellulose is subjected to the desalting treatment with the cation exchange resins followed by the fibrillation treatment thereof. The explanation below will be made about the case that the acid type carboxylated cellulose nanofiber is produced by desalting with cation exchange resins after fibrillation.

[3-1. Oxidation Treatment]

The oxidation treatment is a treatment of preparing the oxidized cellulose by oxidizing a cellulose raw material. The oxidation method thereof is not particularly restricted, but is preferably the method of using an oxidizing agent in the presence of an N-oxyl compound together with a bromide, an iodide or a mixture thereof. When the cellulose raw material is oxidized by this method, it is possible to obtain the constituent unit having the carboxy group formed by selectively oxidizing the carbon atom having a primary hydroxy group at the C6 position of the glucopyranose constituting the cellulose molecular chain.

The partial structure of the oxidized cellulose obtained by this method is illustrated in the following general formula (1).

[Chem. 2]

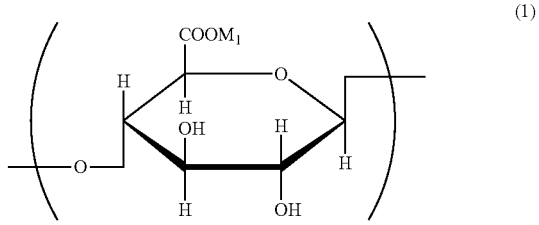

(1)

(In the general formula (1), $M_1$ represents a cationic salt.)

In the general formula (1), examples of the cationic salt represented by $M_1$ include the alkali metal salt such as a sodium salt and a potassium salt, a phosphonium salt, an imidazolinium salt, an ammonium salt, and a sulfonium salt.

A natural cellulose has a microfibril structure in which a large number of linear cellulose molecular chains are converged by the hydrogen bond. When the cellulose is oxidized by using the N-oxyl compound, the carbon atom having a primary hydroxy group at the C6 position of the glucopyranose constituting the cellulose molecular chain is selectively oxidized to the carboxy group via an aldehyde group, as described above. Therefore, the carboxy groups are introduced onto the surface of the microfibril structure with a high density. The introduced carboxy groups have a repulsive action so that the cellulose nanofibers separated into individual fibers can be obtained by fibrillation.

Examples of the cellulose raw material include a kraft pulp or a sulfite pulp derived from wood, powdered cellulose obtained by crushing these pulps with a high pressure homogenizer, a mill, or the like, and a microcrystalline cellulose powder obtained by refining these pulps with a chemical treatment such as acid hydrolysis. Besides these, the cellulose raw materials derived from plants such as kenaf, hemp, rice, bagasse, and bamboo may also be used. In view of mass production and cost, powdered cellulose, microcrystalline cellulose powder, or a chemical pulp such as a kraft pulp or a sulfite pulp is preferably used. When the chemical pulp is used, it is preferable to remove a lignin by a heretofore known bleaching treatment. As the bleached pulp, for example, the bleached kraft pulp or the bleached sulfite pulp having the whiteness (ISO 2470) of 80% or higher may be used.

The powdered cellulose is a rod axis-like particle formed of microcrystalline or crystalline cellulose, which is obtained by removing the amorphous portion of wood pulp by acid hydrolysis and thereafter performing pulverization and sieving. In the powdered cellulose, the degree of polymerization of the cellulose is from about 100 to about 500, the crystallinity of the powdered cellulose measured with an X-ray diffraction method is from 70 to 90%, and the volume-average particle diameter measured with a laser diffraction-type particle diameter distribution measurement apparatus is usually 100 µm or smaller, and preferably 50 µm or smaller. Such powdered cellulose may be prepared by refining and drying an unhydrolyzed residue obtained after the acid hydrolysis of a selected pulp followed by crushing and sieving, or alternatively, a commercially available product such as KC Flock (registered trade mark) (manufactured by Nippon Paper Industries Co., Ltd.), Ceolus (registered trade mark) (manufactured by Asahi Kasei Chemicals Corp.), or Avicel (registered trade mark) (manufactured by FMC Corp.) may also be used.

The bleaching treatment method may be carried out by combinations of a chlorine treatment (C), a chlorine dioxide bleaching (D), an alkali extraction (E), a hypochlorite salt bleaching (H), a hydrogen peroxide bleaching (P), an alkali hydrogen peroxide treatment stage (Ep), an alkali hydrogen peroxide-oxygen treatment stage (Eop), an ozone treatment (Z), a chelate treatment (Q), and the like. For example, the bleaching method may be performed at the sequence such as C/D-E-H-D, Z-E-D-P, Z/D-Ep-D, Z/D-Ep-D-P, D-Ep-D, D-Ep-D-P, D-Ep-P-D, Z-Eop-D-D, Z/D-Eop-D, or Z/D-Eop-D-E-D. Note that "/" in the sequences means that the treatments before and after "/" are carried out continuously without washing.

Alternatively, the micronized materials of the aforementioned cellulose raw materials by using a disperser such as a high speed rotation type, a colloid mill type, a high pressure type, a roll mill type, or an ultrasonic wave type, or a wet type high pressure or ultrahigh pressure homogenizer, or the like, may be used as the cellulose raw material.

The N-oxyl compound is the compound capable of generating a nitroxy radical. Any N-oxyl compound may be used so far as the compound capable of effecting an intended oxidation reaction. Examples of the N-oxyl compound include compounds represented by the following general formulae (2) to (5) and (7), and the compound represented by the following formula (6).

[Chem. 3]

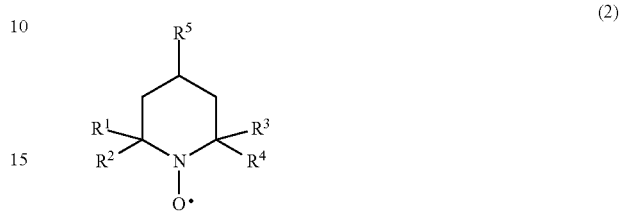

(2)

(In the general formula (2), $R^1$ to $R^4$ represent the same or different alkyl group having 1 to 4 carbon atoms, and $R^5$ represents a hydrogen atom or a hydroxy group.)

[Chem. 4]

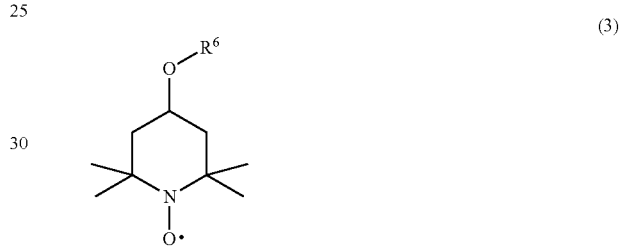

(3)

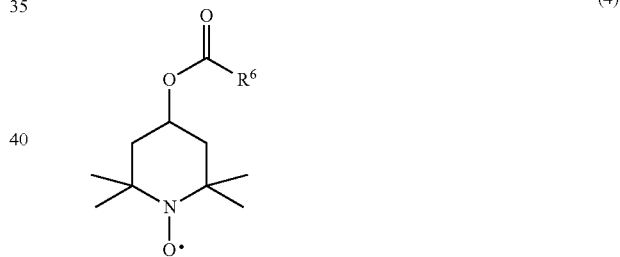

(4)

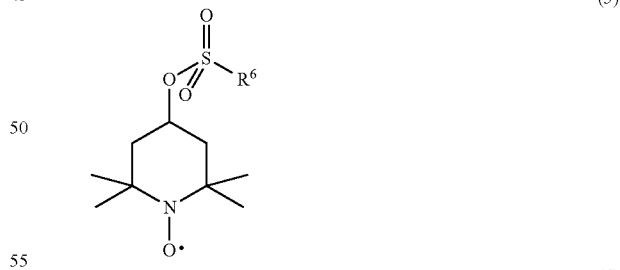

(5)

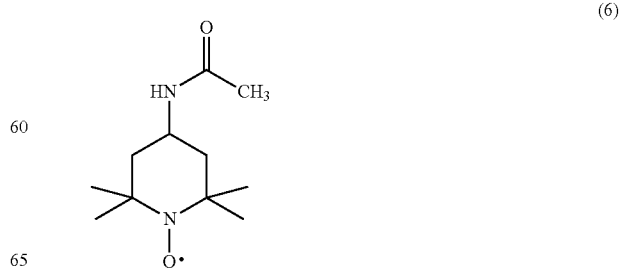

(6)

(In the general formulae (3) to (5), $R^6$ represents a linear or a branched hydrocarbon group having 1 to 4 carbon atoms.)

[Chem. 5]

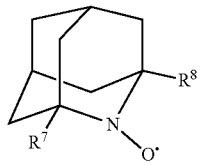

(7)

(In the general formula (7), $R^7$ to $R^8$ represent the same or different hydrogen atom or a linear or a branched alkyl group having 1 to 6 carbon atoms.)

In the general formula (2), examples of the alkyl group having 1 to 4 carbon atoms represented by $R^1$ to $R^4$ include methyl group, ethyl group, propyl group, and butyl group. Among them, methyl group or ethyl group is preferable.

In the general formulae (3) to (5), examples of the linear or the branched hydrocarbon group having 1 to 4 carbon atoms represented by $R^6$ include methyl group, ethyl group, n-propyl group, isopropyl group, n-butyl group, s-butyl group, and t-butyl group. Among them, methyl group or ethyl group is preferable.

In the general formula (7), examples of the linear or the branched alkyl group having 1 to 6 carbon atoms represented by $R^7$ to $R^8$ include methyl group, ethyl group, n-propyl group, isopropyl group, n-butyl group, s-butyl group, t-butyl group, n-pentyl group, and n-hexyl group. Among them, methyl group or ethyl group is preferable.

Examples of the compound represented by the general formula (2) include 2,2,6,6-tetramethyl-1-piperidine-N-oxy radical (hereinafter, this is also called "TEMPO") or 4-hydroxy-2,2,6,6-tetramethyl-1-piperidine-N-oxy radical (hereinafter, this is also called "4-hydroxy TEMPO").

The N-oxyl compound may also be derivatives of TEMPO or of 4-hydroxy TEMPO. Examples of the derivative of 4-hydroxy TEMPO include a compound represented by the general formula (3), that is, a derivative obtained by etherifying the hydroxy group of 4-hydroxy TEMPO with an alcohol having a linear or a branched hydrocarbon group having the carbon number of 4 or less, and a compound represented by the general formula (4) or (5), that is, a derivative obtained by esterifying with a carboxylic acid or a sulfonic acid.

When an alcohol having the carbon number of 4 or less is used upon etherifying 4-hydroxy TEMPO, a derivative to be obtained becomes water soluble regardless of presence or absence of a saturated or an unsaturated bond in the alcohol. As a result, the derivative to be obtained can well function as an oxidant catalyst.

When the N-oxyl compound is the compound represented by the formula (6), that is, the compound of which the amino group of 4-amino TEMPO is acetylated, the oxidized cellulose provided with an appropriate hydrophobicity, and being cheap and uniform can be obtained, which is preferable. Also, when the N-oxyl compound is the compound represented by the general formula (7), that is, an azaadamantane type nitroxy radical, the uniform oxidized cellulose can be obtained in a short period of time, which is preferable.

The used amount of the N-oxyl compound is not particularly restricted as long as the catalyst amount capable of oxidizing the cellulose raw material sufficiently to fibrillate the oxidized cellulose to be obtained till the nanofiber. For example, the amount relative to 1 g of the bone dry cellulose raw material is preferably from 0.01 to 10 mmol, more preferably from 0.01 to 1 mmol, and further preferably from 0.01 to 0.5 mmol.

The bromide to be used at the time of oxidation of the cellulose raw material is a compound having bromine, and examples thereof include alkali metal bromides capable of being dissociated in water to be ionized. The iodide is a compound having iodine, and examples thereof include alkali metal iodides.

The used amount of the bromide or the iodide may be adjusted within the range capable of promoting the intended oxidation reaction. For example, the total amount of the bromide and the iodide relative to 1 g of the bone dry cellulose raw material is preferably from 0.1 to 100 mmol, more preferably from 0.1 to 10 mmol, and further preferably from 0.5 to 5 mmol.

As the oxidant, it may use the heretofore known oxidants such as halogens, hypohalous acids, halous acids, perhalogenated acids, the salts of these acids, halogen oxides, and peroxides. Among these oxidants, sodium hypochlorite is preferable because of cheap and less environmental load.

The used amount of the oxidant may be any so far as the oxidation reaction can take place. For example, the amount thereof relative to 1 g of the bone dry cellulose raw material is preferably from 0.5 to 500 mmol, more preferably from 0.5 to 50 mmol, and further preferably from 2.5 to 25 mmol.

Since the oxidation reaction of the cellulose raw material advances efficiently even under a relatively mild condition, the reaction temperature may be room temperature in the range from about 15° C. to about 30° C. As the reaction progresses, the carboxy groups are formed in the cellulose so that the pH value of the reaction solution decreases. In order to efficiently carry out the oxidation reaction, it is preferable to keep the pH value of the reaction solution from 9 to 12, and preferably from about 10 to about 11 by timely adding an alkali solution such as aqueous sodium hydroxide solution into the reaction system. The reaction medium is preferably water because of easy handling and hardly causing a side reaction.

The reaction time in the oxidation reaction can be arbitrarily determined in accordance with the degree of progress of the oxidation. The reaction time is usually from about 0.5 to about 6 hours, and preferably from about 0.5 to about 4 hours.

The oxidation reaction may be carried out in two stages. For example, the cationic salt of the oxidized cellulose obtained by filtration after completion of the first stage reaction is again oxidized under the same or different reaction condition. Thereby, the carboxy groups can be efficiently introduced into the cellulose raw material without receiving reaction inhibition due to the by-produced salt in the first stage reaction.

In the oxidized cellulose obtained in the above-mentioned process, the carboxy groups introduced into the cellulose raw material are usually an alkali metal salt such as a sodium salt. Before the desalting treatment or the fibrillation treatment to be described later, the alkali metal salt of the oxidized cellulose may be substituted to other cationic salt such as a phosphonium salt, an imidazolinium salt, an ammonium salt, or a sulfonium salt. The substitution may be performed by heretofore known methods.

As the other example of the oxidation method, there may be a method of contacting the cellulose raw material with an ozone-including gas. According to this oxidation reaction, the carbon atoms having hydroxy groups at least of 2- and 6-positions in the glucopyranose ring are oxidized as well as decomposition of the cellulose chain takes place.

The ozone concentration in the ozone-including gas is preferably from 50 to 250 g/m$^3$, and more preferably from 50 to 220 g/m$^3$. The addition amount of ozone to the cellulose raw material on the basis of 100 parts by mass of the solid component in the cellulose raw material is preferably from 0.1 to 30 parts by mass, and more preferably from 5 to 30 parts by mass. The temperature of the ozone treatment is preferably from 0 to 50° C., and more preferably from 20 to 50° C. The time of the ozone treatment is not particularly restricted, but it is usually from about 1 to about 360 minutes, and preferably from about 30 to about 360 minutes. When the conditions of the ozone treatment are within these ranges, it is possible to prevent the excessive oxidation and decomposition of the cellulose to obtain the oxidized cellulose in good yield.

After the ozone treatment, an additional oxidation treatment may be carried out by using an oxidant. The oxidant to be used in the additional oxidation treatment is not particularly restricted. Examples thereof include chlorine-based compounds such as chlorine dioxide and sodium chlorite, oxygen, hydrogen peroxide, persulfuric acid, and peracetic acid. For example, the additional oxidation treatment may be performed in such a manner that an oxidant solution is prepared by dissolving any of these oxidants in water or in a polar organic solvent such as an alcohol, and then the cellulose raw material is soaked into this solution.

It is preferable that the oxidized cellulose obtained by the oxidation treatment is washed before subjected to the alkali hydrolysis treatment to be described later in order to avoid a side reaction. The washing method is not particularly restricted, and it may be performed by heretofore known methods.

[3-2. Fibrillation Treatment]

The fibrillation treatment is the treatment of fibrillating the oxidized cellulose or the alkali hydrolyzed oxidized cellulose. Since the carboxy groups are introduced into the oxidized cellulose or the alkali hydrolyzed oxidized cellulose by the oxidation treatment, it is possible to easily perform the nano-fibrillation by the fibrillation treatment.

As the fibrillation treatment, it may be carried out, for example, by using a heretofore known apparatus such as a high speed shear mixer or a high pressure homogenizer after sufficiently washing the oxidized cellulose or the alkali hydrolyzed oxidized cellulose with water. Examples of the kinds of the fibrillation apparatus include a high speed rotation type, a colloid mill type, a high pressure type, a roll mill type, and an ultrasonic wave type. These apparatuses may be used alone, or as a combination of two or more of them.

When the high speed shear mixer is used, the shearing speed is preferably 1,000 sec$^{-1}$ or faster. When the shearing speed is 1,000 sec$^{-1}$ or faster, the agglomerate structure can be suppressed to perform the nano-fibrillation uniformly.

When the high pressure homogenizer is used, the pressure to be applied is preferably 50 MPa or higher, more preferably 100 MPa or higher, and further preferably 140 MPa or higher. When the treatment is carried out at this pressure with a wet-type high pressure or an ultrahigh pressure homogenizer, the nano-fibrillation is efficiently progressed to obtain the carboxylated cellulose nanofiber efficiently.

The oxidized cellulose or the alkali hydrolyzed oxidized cellulose is subjected to the fibrillation treatment as water dispersion such as water. When the concentration of the oxidized cellulose or the alkali hydrolyzed oxidized cellulose in the water dispersion is too high, the viscosity sometimes excessively increases during the fibrillation treatment. Thus, it cannot sometimes fibrillate uniformly, or the apparatus sometimes stops. Accordingly, the concentration of the oxidized cellulose or the alkali hydrolyzed oxidized cellulose needs to be appropriately determined in accordance with the treatment condition of the oxidized cellulose or the alkali hydrolyzed oxidized cellulose. As one example, the concentration of the oxidized cellulose or the alkali hydrolyzed oxidized cellulose is preferably from 0.3 to 50% (w/v), more preferably from 0.5 to 10% (w/v), and further preferably from 1.0 to 5% (w/v).

[3-3. Alkali Hydrolysis Treatment]

The alkali hydrolysis treatment is a treatment of preparing the hydrolyzed oxidized cellulose by hydrolyzing oxidized cellulose obtained by the above oxidation treatment in alkali solution. The acid type carboxylated cellulose nanofiber obtained by this treatment is the nanofiber B. In view of suppression of a side reaction, the reaction medium of the hydrolysis treatment is preferably water.

By performing the hydrolysis in the alkali solution, the nanofiber B is shortened in the fiber length thereof to satisfy the numerical range defined in the present application. The reason for this is presumed as follows. The carboxy groups are dispersed in an amorphous region of the oxidized cellulose oxidized by using the N-oxyl compound. Therefore, the hydrogen atoms at the C5 position that is adjacent to these carboxy groups are in the state of lacking an electric charge because the electron thereof is withdrawn by the carboxy groups. Therefore, these hydrogen atoms are readily pulled out by the hydroxide ions in the alkali condition of pH 8 to 14 thereby causing breakage of the glucoside bond by a β-elimination reaction. As a result, the shortening fibrillation is made to the oxidized cellulose to increase the ratio of the carboxylated cellulose nanofiber having a short fiber length.

When the hydrolysis is carried out in the alkali solution, the pH value of the reaction solution in the reaction is preferably from 8 to 14, more preferably from 9 to 13, and further preferably from 10 to 12. When the pH value is lower than 8, the hydrolysis reaction does not take place sufficiently so that the shortening fibrillation of the oxidized cellulose may be insufficient in some cases. On the other hand, when the pH value is higher than 14, the hydrolysis may advance, but the oxidized cellulose after the hydrolysis may be colored. Therefore, since the obtained cellulose nanofiber may also be colored, the transparency thereof decreases to cause a problem of restricting the technology to be applied in some cases. The alkali to be used for adjustment of the pH value may be any substance as long as it is water-soluble, and sodium hydroxide is preferable in view of manufacturing cost.

When the oxidized cellulose is hydrolyzed in the alkali solution, the oxidized cellulose can be colored to a yellow color due to the formation of a double bond upon the β-elimination. Therefore, since the cellulose nanofiber to be obtained is also colored, the transparency thereof decreases to restrict the technology to be applied in some cases. Accordingly, in order to suppress the formation of the double bond, the hydrolysis process is preferably carried out by using an oxidant or a reductant as an auxiliary agent. When the oxidant or the reductant is used at the time of the hydrolysis treatment in the alkali solution of pH 8 to 14, it is possible to perform the shortening fibrillation of the oxidized cellulose while oxidizing or reducing the double bond. As the oxidant or the reductant, the substances having their activities in the alkali region may be used.

In view of the reaction efficiency, the addition amount of the auxiliary agent relative to the bone dry oxidized cellulose is preferably from 0.1 to 10% by mass, more preferably from 0.3 to 5% by mass, and further preferably from 0.5 to 2% by mass.

Examples of the oxidant include oxygen, ozone, hydrogen peroxide, and hypochlorite salts. Among them, the oxidant is preferably oxygen, hydrogen peroxide, and hypochlorite salts, which are difficult to generate a radical, and more preferably hydrogen peroxide.

These oxidants may be used alone, or as a mixture of two or more of them.

Examples of the reductant include sodium borohydride, hydrosulfite, and sulfite salts.

These reductants may be used alone, or as a mixture of two or more of them.

In view of the reaction efficiency, the reaction temperature of the hydrolysis is preferably from 40 to 120° C., more preferably from 50 to 100° C., and further preferably from 60 to 90° C. When the temperature is low, the hydrolysis may not take place sufficiently to cause a case where the shortening fibrillations of the oxidized cellulose or of the carboxylated cellulose nanofiber can be insufficient, in some cases. On the other hand, when the temperature is high, the hydrolysis may advance, but the oxidized cellulose after the hydrolysis may be colored.

The reaction time of the hydrolysis is preferably from 0.5 to 24 hours, more preferably from 1 to 10 hours, and further preferably from 2 to 6 hours.

In view of the reaction efficiency, the concentration of the oxidized cellulose in the alkali solution is preferably from 1 to 20% by mass, more preferably from 3 to 15% by mass, and further preferably from 5 to 10% by mass.

[3-4. Desalting Treatment]

The desalting treatment is a treatment of desalting the fibrillated oxidized cellulose or the alkali hydrolyzed oxidized cellulose (carboxylated cellulose nanofiber salt) with cation exchange resins. With this treatment, the cationic salt of the fibrillated oxidized cellulose or of the alkali-hydrolyzed oxidized cellulose is substituted with the proton to obtain the acid-type carboxylated cellulose nanofiber. Since the cation exchange resins are used, unnecessary by-products such as sodium chloride are not produced. Accordingly, after the desalting treatment by using the cation exchange resins, the water dispersion of the acid-type carboxylated cellulose nanofiber substituted with proton can be obtained as filtrate only by filtering out the cation exchange resins through a metal mesh or the like.

The object to be removed as the filtered material through a metal mesh or the like is the cation exchange resins. The carboxylated cellulose nanofiber is hardly removed through a diameter of the metal mesh or the like. Therefore, an almost entire amount of the nanofiber is included in the filtrate. Accordingly, the decrease in the yield is very small.

A large amount of the carboxylated cellulose nanofiber having a short fiber length is included in the filtrate. In addition, since it is not necessary to wash or dehydrate the filtrate, the acid-type carboxylated cellulose nanofiber is hardly agglomerated. Accordingly, in the case where the alkali hydrolysis treatment is not done, it is presumed that the viscosity of the dispersion liquid of the carboxylated cellulose nanofiber is high in the low shear region. On the other hand, when the alkali hydrolysis treatment is done, the acid-type carboxylated cellulose nanofiber having a very short fiber length can be isolated.

As the carboxylated cellulose nanofiber salt, the water dispersion thereof obtained in the fibrillation process may be provided directly to the desalting process. Incidentally, the concentration thereof may be lowered by adding water when necessary.

As the cation exchange resins, any of a strong acid ion exchange resin and a weak acid ion exchange resin may be used as long as the counter ion thereof is $H^+$. Among these, the strong acid ion exchange resin is preferably used. Examples of the strong acid ion exchange resin and the weak acid ion exchange resin include a styrene-based resin or an acryl-based resin to which a sulfonic acid group or a carboxy group is introduced.

The shape of the cation exchange resin is not particularly restricted, and may be various shapes such as granules (particulate), membranes, and fibers. Among these, in view of efficient desalting of the carboxylated cellulose nanofiber salt and facilitating the separation after the desalting treatment, the particulate is preferable. As such a cation exchange resin, commercially available products may be used. Examples of the commercially available product include Amberjet 1020, 1024, 1060, and 1220 (manufactured by Organo Corp.), Amberlite IR-200C and IR-120B (manufactured by Tokyo Organic Chemicals Industries Ltd.), Lewatit SP112 and S100 (manufactured by Bayer AG), GEL CK08P (manufactured by Mitsubishi Chemical Corp.), and Dowex 50W-X8 (manufactured by The Dow Chemical Company).

The desalting treatment may be carried out as follows. For example, while stirring and shaking as necessary, the particulate cation exchange resins and the water dispersion of the carboxylated cellulose nanofiber salt are mixed to bring the carboxylated cellulose nanofiber salt into contact with the cation exchange resins for a certain period of time, and thereafter the cation exchange resins and the water dispersion are separated.

The concentration of the water dispersion and the ratio of the water dispersion to the cation exchange resins are not particularly restricted, and the skilled person in the art can appropriately determine them in view of an efficient substitution with the protons. In one example, the concentration of the water dispersion is preferably from 0.05 to 10% by mass. When the concentration of the water dispersion is lower than 0.05% by mass, the time necessary for substitution with the protons may take too long. When the concentration of the water dispersion is higher than 10% by mass, the sufficient effect of the substitution with the protons may not be exerted.

Also, the contact time is not particularly restricted, and the skilled person in the art can appropriately determine it in view of an efficient substitution with the protons. For example, it can be carried out by contacting with the resins for 0.2 to 0.4 hours.

At this time, the desalting treatment can be carried out in such a manner that an appropriate amount of the cation exchange resins is placed in contact with the carboxylated cellulose nanofiber salt or with the oxidized cellulose for a sufficient period of time, and thereafter the cation exchange resins are removed as the residue thorough a metal mesh or the like.

[3-5. Shortening Fibrillation Treatment]

When the nanofiber B of the present invention is produced, a shortening fibrillation treatment may be carried out after the oxidation treatment or the alkali hydrolysis treatment, and before the fibrillation treatment. By carrying out such a treatment, the nanofiber B having a further shorter fiber length can be obtained.

The shortening fibrillation treatment is a treatment of performing the shortening fibrillation by cutting the cellulose chain of the oxidized cellulose or of the alkali hydrolyzed oxidized cellulose properly. Examples of the treatment include an ultraviolet irradiation treatment, an oxidative decomposition treatment, and an acid hydrolysis treatment. Among them, an acid hydrolysis treatment is preferable.

These treatments may be carried out alone, or as a combination of two or more of them.

The acid hydrolysis treatment is a treatment of hydrolyzing the oxidized cellulose or the alkali hydrolyzed oxidized cellulose in acidic solution.

By carrying out the hydrolysis treatment in acidic solution, it is possible to subject the carboxylated cellulose nanofiber to the shortening fibrillation. The reason may be presumed as follows. On the surface of the cellulose raw material oxidized by using the N-oxyl compound, the carboxy groups are localized, and the hydrated layer is formed there. Therefore, the oxidized celluloses exist in proximity with each other to form the network. When the hydrolysis is performed by addition of acid to the oxidized celluloses, the balance among charges in the network may be lost so that the strong network among cellulose molecules is lost. As a result, the specific surface area of the oxidized cellulose increases to promote the shortening fibrillation of the oxidized cellulose. Accordingly, since the fiber of the oxidized cellulose is shortened, the ratio of the carboxylated cellulose nanofiber having a short fiber length increases.

When the hydrolysis is carried out in acidic solution, the mineral acid such as sulfuric acid, hydrochloric acid, nitric acid, or phosphoric acid is preferably used. In addition, in order to efficiently carry out the reaction, it is preferable to use dispersion liquid prepared by dispersing the oxidized cellulose into dispersing medium such as water.

As the condition of the hydrolysis in the acidic solution, it may be any condition under which the acid can act to the amorphous portion of the cellulose. For example, the addition amount of the acid relative to the bone dry mass of the oxidized cellulose is preferably from 0.01 to 0.5% by mass, and more preferably from 0.1 to 0.5% by mass. When the addition amount of the acid is 0.01% by mass or larger, the hydrolysis of the cellulose advances to improve the treatment efficiency in the fibrillation process, which is preferable. When the addition amount thereof is 0.5% by mass or smaller, the excessive hydrolysis of the cellulose can be suppressed to prevent the decrease of the yield of the cellulose nanofiber.

When the hydrolysis is carried out in the acidic solution, the pH value of the reaction solution during the reaction is preferably from 2.0 to 4.0, and more preferably 2.0 or higher and lower than 3.0. In view of the reaction efficiency, it is preferable that the reaction temperature is from 70 to 120° C., and the reaction time is from 1 to 10 hours.

When the hydrolysis has been carried out in the acidic solution, the solution is usually neutralized by adding an alkali such as sodium hydroxide for the purpose of efficiently carrying out the fibrillation process.

The ultraviolet irradiation treatment is a treatment of irradiating the oxidized cellulose or the alkali hydrolyzed oxidized cellulose with ultraviolet rays. By irradiation with ultraviolet rays, it is possible to perform the shortening fibrillation of the carboxylated cellulose nanofiber. The reason may be presumed as follows. The ultraviolet rays directly acts on celluloses or hemicelluloses to make them low molecules. Thus, the shortening fibrillation of the cellulose chain in the oxidized cellulose can be performed. Accordingly, the ratio of the carboxylated cellulose nanofiber having a short fiber length also increases.

When the oxidized cellulose or the alkali hydrolyzed oxidized cellulose is irradiated with the ultraviolet rays, the wavelength of the ultraviolet rays to be used is preferably from 100 to 400 nm, and more preferably from 100 to 300 nm. Among these, the ultraviolet rays having a wavelength from 135 to 260 nm are preferable, because such ultraviolet rays directly act on celluloses or hemicelluloses to make them low molecules, and thus the shortening fibrillation of the cellulose chain in the oxidized cellulose can be performed.

As the light source for the irradiation with ultraviolet rays, the light sources having the light in the wavelength region from 100 to 400 nm may be used. Examples thereof include a xenon short arc lamp, an ultrahigh pressure mercury lamp, a high pressure mercury lamp, a low pressure mercury lamp, a deuterium lamp, and a metal halide lamp.

The light source may be used alone, and two or more types thereof may also be used in combination. Since the simultaneous irradiation with ultraviolet rays having different wavelengths increases the number of cut portions in the cellulose chain or the hemicellulose chain to prompt the shortening fibrillation, the use of multiple light sources having different wavelength characteristics in combination is preferable.

As the container to place the oxidized cellulose during ultraviolet irradiation, for example when the ultraviolet rays having the wavelength from 300 to 400 nm is used, it may be a hard glass container. When the ultraviolet rays having a short wavelength of less than 300 nm is used, it is preferable to use a quartz glass container capable of further transmitting the ultraviolet rays. The material of the container portion not involved in the light transmission reaction may be appropriately selected from the materials that are less likely to deteriorate due to the wavelength of the ultraviolet rays to be used.

The concentration of the oxidized cellulose when irradiated with ultraviolet rays is preferably from 0.1 to 12% by mass, more preferably from 0.5 to 5% by mass, and further preferably from 1 to 3% by mass. When the concentration of the oxidized cellulose is 0.1% by mass or higher, the energy efficiency is enhanced, which is preferable. When the concentration of the oxidized cellulose is 12% by mass or lower, the fluidity of the oxidized cellulose in the ultraviolet irradiation apparatus is so good that the reaction efficiency is enhanced, which is preferable.

The temperature at the time of irradiation with ultraviolet rays is preferably from 20 to 95° C., more preferably from 20 to 80° C., and further preferably from 20 to 50° C. When the temperature is 20° C. or higher, the efficiency of the photo oxidation reaction is enhanced, which is preferable. When the temperature is 95° C. or lower, there is no possibility of adverse influences such as deterioration of the quality of the oxidized cellulose, and there is no possibility that the pressure in the reaction apparatus will exceed the atmospheric pressure. Therefore, it is unnecessary to design an apparatus in consideration of pressure resistance, which are preferable.

The pH value at the time of irradiation with ultraviolet rays is not particularly restricted, but from the viewpoint of simplifying the process, it is preferable that it is the neutral region, for example, the pH value is from about 6.0 to about 8.0.

The degree of irradiation applied to the oxidized cellulose during ultraviolet irradiation may be arbitrarily determined by adjusting the residence time of the oxidized cellulose in the irradiation reaction apparatus, or by adjusting the energy amount of the irradiation light source, and the like. In addition, the ultraviolet irradiation amount applied to the oxidized cellulose in the irradiation reaction apparatus may be arbitrarily controlled by adjusting the concentration of the oxidized cellulose in the irradiation apparatus by dilution with water, by adjusting the concentration of the oxidized cellulose by blowing an air or an inert gas such as a nitrogen gas into the oxidized cellulose, or the like. These conditions such as the residence time and the concentration may be appropriately set depending on the intended quality (such as the fiber length and the polymerization degree of cellulose) of the oxidized cellulose after ultraviolet irradiation.

When the ultraviolet irradiation treatment is performed in the presence of an auxiliary agent such as oxygen, ozone, and a peroxide (hydrogen peroxide, peracetic acid, sodium percarbonate, sodium perboric acid, and the like), the efficiency of the photooxidation reaction is enhanced, which is preferable.

When irradiated with ultraviolet rays having wavelength region from 135 to 242 nm, ozone is generated from the air existing in the gas phase around the light source. The generated ozone is continuously removing while continuously supplying air to the periphery of the light source, and then the removed ozone is injected into the oxidized cellulose. Thereby, this ozone may also be utilized as the auxiliary agent for the photo oxidation reaction without supplying the ozone from outside the system. In addition, by supplying oxygen to the gas phase portion around the light source, a larger amount of ozone can be generated in the system, and the generated ozone may also be used as the auxiliary agent for the photo oxidation reaction. In this manner, the ozone secondarily generated in the ultraviolet irradiation reaction apparatus may also be utilized.

The ultraviolet irradiation treatment may be repeated plural times. The number of repeat is not particularly restricted, and may be appropriately determined depending on the relationship with, for example, the intended quality of the oxidized cellulose. For example, the ultraviolet irradiation can be performed with ultraviolet rays at preferably from 100 to 400 nm, and more preferably from 135 to 260 nm, preferably from 1 to 10 times, and more preferably from 2 to 5 times, and for the irradiation time per one repeat of preferably for 0.5 to 10 hours, and more preferably for 0.5 to 3 hours.

When the oxidized cellulose is subjected to the oxidative decomposition treatment, hydrogen peroxide and ozone are usually used in combination.

It is inferred that the reason why the use of hydrogen peroxide and ozone in combination can efficiently perform the shortening fibrillation of the oxidized cellulose is as follows. On the surface of the oxidized cellulose produced by oxidation using the N-oxyl compound, the carboxy groups are localized, and a hydrated layer is formed. Therefore, it is considered that there is a microscopic space, which is not observed in normal cellulose, between the cellulose chains of the oxidized cellulose due to the action of the charge repelling force between the carboxy groups. When the oxidized cellulose is treated with ozone and hydrogen peroxide, a hydroxy radical having excellent oxidation power is generated from ozone and hydrogen peroxide. The hydroxy radical efficiently oxidizes and decomposes the cellulose chain in the oxidized cellulose to eventually perform the shortening fibrillation of the oxidized cellulose. Accordingly, the ratio of the carboxylated cellulose nanofiber having a short fiber length increases.

Ozone can be generated by a known method with an ozone generator and using air or oxygen as a raw material. The addition amount (in terms of mass) of the ozone relative to the bone dry mass of the oxidized cellulose is preferably from 0.1 to 3 times, more preferably from 0.3 to 2.5 times, and further preferably from 0.5 to 1.5 times. When the addition amount of the ozone relative to the bone dry mass of the oxidized cellulose is 0.1 time or larger, the amorphous portion of the cellulose can be sufficiently decomposed. When the addition amount of the ozone relative to the bone dry mass of the oxidized cellulose is 3 times or smaller, the excessive decomposition of the cellulose can be suppressed, and the lowering of the yield of the oxidized cellulose can be prevented.

The addition amount (in terms of mass) of the hydrogen peroxide relative to the bone dry mass of the oxidized cellulose is preferably from 0.001 to 1.5 times, and more preferably from 0.1 to 1.0 times. When the addition amount of the hydrogen peroxide relative to the bone dry mass of the oxidized cellulose is 0.001 time or larger, a synergistic effect between the ozone and the hydrogen peroxide is exerted. It is sufficient for decomposition of the oxidized cellulose to add the hydrogen peroxide in an amount of 1.5 times or smaller relative to the oxidized cellulose. Adding the hydrogen peroxide in an amount of exceeding 1.5 times leads to increase a cost, which is not preferable.

As the conditions of the oxidative decomposition treatment with ozone and hydrogen peroxide, the pH value is preferably from 2 to 12, more preferably from 4 to 10, and further preferably from 6 to 8, the temperature is preferably from 10 to 90° C., more preferably from 20 to 70° C., and further preferably from 30 to 50° C., and the reaction time is preferably from 1 to 20 hours, more preferably from 2 to 10 hours, and further preferably from 3 to 6 hours, from the viewpoint of reaction efficiency.

The apparatus for performing the treatment with ozone and hydrogen peroxide is not particularly restricted, and may be any heretofore known apparatus. Example thereof includes a usual reaction vessel provided with a reaction chamber, a stirrer, a chemical injector, a heater, and a pH electrode.

After the treatment with ozone and hydrogen peroxide, the ozone and the hydrogen peroxide remained in the aqueous solution can also effectively act in the fibrillation process to further promote the lowering of the viscosity of the dispersion liquid of the carboxylated cellulose nanofiber.

[4. Uses]

The nanofiber A of the present invention can be used in spray compositions, rubber reinforcing materials, resin reinforcing materials, cosmetics, medicinal products, foods, beverages, paints, and the like. Among them, it is preferable to use in spray compositions utilizing the characteristic of high viscosity in the low shear region.

(Spray Composition)

The spray composition includes the nanofiber A described above and water. The spray composition may include a functional additive in accordance with the use of the spray.

Since the nanofiber A has a high viscosity in the low shear region, the spray composition can prevent the dripping without separately blending a thickener or with blending a very small amount of a thickener.

Examples of the functional additive include a surfactant, oils, a moisturizing agent, an organic microparticle, an inorganic microparticle, a preservative, a deodorant, a flavor, and an organic solvent. These can be selected in accordance with the use of the spray composition.

These functional additives may be used alone, or as a combination of two or more of them.

Examples of a nonionic surfactant include a propylene glycol fatty acid ester, a glycerin fatty acid ester, a polyoxyethylene glycerin fatty acid ester, a polyglycerin fatty acid ester, a sorbitan fatty acid ester, a polyethylene glycol fatty acid ester, a polyoxyethylene castor oil, a polyoxyethylene hardened castor oil, a polyoxyethylene alkyl ether, a polyoxyethylene phytosterol, a polyoxyethylene polyoxypropylene alkyl ether, a polyoxyethylene alkylphenyl ether, polyoxyethylene lanolin, polyoxyethylene lanolin alcohol, a polyoxyethylene beeswax derivative, a polyoxyethylene alkylamine, a polyoxyethylene fatty acid amide, and a polyoxyethylene alkylphenyl formaldehyde condensate.

Examples of the oils include naturally animal and plant fats and oils such as a jojoba oil, a macadamia nut oil, an avocado oil, an evening primrose oil, a mink oil, a canola oil, a castor oil, a sunflower oil, a corn oil, a cacao oil, a coconut oil, a rice bran oil, an olive oil, an almond oil, a sesame oil, a safflower oil, a soybean oil, a camellia oil, a persic oil, a cottonseed oil, a Japan wax, a palm oil, a palm kernel oil, an egg yolk oil, lanolin, and squalene; hydrocarbons such as a synthetic triglyceride, squalene, a liquid paraffin, vaseline, ceresin, a microcrystalline wax, and an isoparaffin; waxes such as a carnauba wax, a paraffin wax, a whale wax, a beeswax, a candelilla wax, and lanolin; higher alcohols (such as cetanol, stearyl alcohol, lauryl alcohol, cetostearyl alcohol, oleyl alcohol, behenyl alcohol, lanolin alcohol, hydrogenated lanolin alcohol, hexyldecanol, and octyldodecanol); higher fatty acids such as lauric acid, myristic acid, palmitic acid, stearic acid, behenic acid, isostearic acid, oleic acid, linolenic acid, linoleic acid, oxystearic acid, undecylenic acid, a lanolin fatty acid, a hardened lanolin fatty acid, and a soft lanolin fatty acid; cholesterol and derivatives thereof such as cholesteryl-octyldodecyl-behenyl; esters such as isopropyl myristate, isopropyl palmitate, isopropyl stearate, glycerol 2-ethylhexanoate, and butyl stearate; polar oils such as diethylene glycol monopropyl ether, polyoxyethylene polyoxypropylene pentaerythritol ether, polyoxypropylene butyl ether, and ethyl linoleate; and silicones such as an amino-modified silicone, an epoxy-modified silicone, a carboxy-modified silicone, a carbinol-modified silicone, a methacryl-modified silicone, a mercapto-modified silicone, a phenol-modified silicone, a one-terminal reactive silicone, a heterogonous functional group-modified silicone, a polyether-modified silicone, a methylstyryl-modified silicone, an alkyl-modified silicone, a higher fatty acid ester-modified silicone, a hydrophilic special modified silicone, a higher alkoxy-modified silicone, a higher fatty acid-including silicone, and a fluorine-modified silicone.

Here, specific examples of the silicones include dimethyl polysiloxane, methyl phenyl polysiloxane, methyl polysiloxane, octamethylcyclo tetrasiloxane, decamethylcyclo pentasiloxane, dodecamethyl cyclohexane siloxane, methylcyclo polysiloxane, octamethyl trisiloxane, decamethyl tetrasiloxane, polyoxyethylene-methyl polysiloxane copolymers, polyoxypropylene-methyl polysiloxane copolymers, poly(oxyethylene-oxypropylene)methyl polysiloxane copolymers, methyl hydrogen polysiloxane, tetrahydro tetramethylcyclo tetrasiloxane, stearoxymethyl polysiloxane, cetoxymethyl polysiloxane, a methyl polysiloxane emulsion, highly polymerized methyl polysiloxane, trimethylsiloxy silicic acid, crosslinked methyl polysiloxane, and crosslinked methyl phenyl polysiloxane.

Examples of the moisturizing agent include polyhydric alcohols such as glyceryl trioctanoate, maltitol, sorbitol, glycerin, propylene glycol, 1,3-butylene glycol, polyethylene glycol, and glycol; organic acids and the salts thereof such as sodium pyrrolidonecarboxylate, sodium lactate, and sodium citrate; hyaluronic acid and the salts thereof such as sodium hyaluronate; yeast and hydrolysates of the yeast extract; fermentation metabolites such as yeast culture solution and lactic acid bacteria culture solution; water-soluble proteins such as collagen, elastin, keratin, and sericin; peptides and the salts thereof such as collagen hydrolysates, casein hydrolysates, silk hydrolysates, and sodium polyaspartate; saccharides, polysaccharides, and the derivatives thereof such as trehalose, xylobiose, maltose, sucrose, glucose, and plant mucopolysaccharides; glucosaminoglycan and the salts thereof such as water-soluble chitin, chitosan, pectin, and chondroitin sulfuric acid and the salt thereof; amino acids such as glycine, serine, threonine, alanine, aspartic acid, tyrosine, valine, leucine, arginine, glutamine, and proline acid; saccharide amino acid compounds such as an aminocarbonyl reaction product; plant extract liquid such as aloe and marronnier, trimethyl glycine, urea, uric acid, ammonia, lecithin, lanolin, squalane, squalene, glucosamine, creatinine, and nucleic acid-related substances such as DNA and RNA.

Examples of the organic microparticle include a latex and an emulsion obtained by emulsion polymerization such as a styrene-butadiene copolymer based latex and an acryl based emulsion, as well as polyurethane water dispersion.

Examples of the inorganic microparticle include zeolite, montmorillonite, asbestos, smectite, mica, fumed silica, colloidal silica, and titanium oxide.

Examples of the preservative include methyl paraben and ethyl paraben.

Examples of the deodorant and the flavor include D-limonene, decylaldhyde, menton, pulegone, eugenol, cinnamaldehyde, benzaldehyde, menthol, peppermint oil, lemon oil, orange oil, and deodorant active ingredients extracted from plant organs (for example, deodorant active ingredients extracted, by water or a hydrophilic organic solvent, from organs of oxalis, houttuynia, Japanese hemlock, ginkgo, Japanese black pine, Japanese red pine, paulownia, fortune tea olive, lilac, orange osmanthus, butterbur, Japanese silverleaf, and forsythia).

Examples of the organic solvent include water-soluble alcohols (such as methanol, ethanol, isopropanol, isobutanol, sec-butanol, tert-butanol, methyl cellosolve, ethyl cellosolve, ethylene glycol, and glycerin), ethers (such as ethylene glycol dimethyl ether, 1,4-dioxane, and tetrahydrofuran), ketones (such as acetone and methyl ethyl ketone), N,N-dimethyl formamide, N,N-dimethyl acetamide, and dimethyl sulfoxide.

The nanofiber B of the present invention can be used for a spray composition; reinforcing materials for rubbers such as NR, SBR, EPDM, and NBR; reinforcing materials for resins such as a polyolefin resin, an acryl resin, a urethane resin, a PVC resin, a polyamide resin, and a PC resin; cosmetics being applied for epithelium such as cream, lotion, gel, stick, pump spray, aerosol, antiperspirants of a roll-on type, deodorants, fragrance-releasing gel, lip sticks, lip gloss, and liquid cosmetic products; medicinal products such as additives to control, to sustain, or to delay drug release, disintegrants for tablets, liquid-retaining agents in scar-caring products and the like, and rheology modifiers; foods such as stabilizers to suppress the creaming or the precipitation in a rheology modifier and a suspension and resistant food fibers; beverages; paints; and metal absorbents for environmentally unfriendly metal included in soil or in drainage water.

EXAMPLES

Hereinafter, the present invention will be explained in more detail by Examples. Examples described below are to properly explain the present invention, so that they do not limit the present invention. Note that the measurement methods of the values or the like of the physical properties are those described above unless otherwise specifically described.

[Viscosity (Pa·s)]

Water was added to the carboxylated cellulose nanofiber to prepare the water dispersion with the concentration from 0.95 to 1.05% by mass. And then, viscosity of this water dispersion was measured at a prescribed shear velocity by using a viscoelastic rheometer.

[Amount of Carboxy Group]

The amount of the carboxy group was measured in the manner as described below. After 60 mL of the carboxylated cellulose slurry (water dispersion) with the concentration of 0.5% by mass was prepared, the pH value thereof was adjusted to 2.5 by adding 0.1 M aqueous hydrochloric acid solution. Thereafter, 0.05 N aqueous sodium hydroxide solution was added thereto dropwise until pH reached 11 while measuring an electric conductivity. From the amount of the sodium hydroxide (a) consumed in the weakly acidic neutralization stage in which the change of the electric conductivity was moderate, the amount of the carboxy group was calculated by using the following equation:

Amount of carboxy group [mmol/g carboxylated cellulose]=a [mL]×0.05/mass of carboxylated cellulose [g].

[Average Fiber Length (nm)]

The carboxylated cellulose nanofiber was fixed onto a mica cut peace, and the lengths of 200 fibers thereof were measured by using an atomic force microscope (AFM) to calculate the length (weighted) average fiber length. Here, the measurement of the fiber length was by using an image analysis software WinROOF (manufactured by Mitani Corp.).

[Average Fiber Diameter (nm)]

The carboxylated cellulose nanofiber water dispersion was prepared by diluting the carboxylated cellulose nanofiber so as to give the concentration thereof of 0.001% by mass. This diluted dispersion liquid was thinly spread on a mica-made sample plate, and the resultant was dried by heating at 50° C. to produce the observation sample. The section height of the shape image observed with an atomic force microscope (AFM) was measured, to calculate the weighted average fiber diameter.

[Ratio of Fibers Having the Fiber Length of 300 Nm or Shorter, or 600 nm or Longer (%)]

In the the carboxylated cellulose nanofiber whose length (weighted) average fiber length was measured, the ratio of fibers having the fiber length of 300 nm or shorter, or 600 nm or longer was calculated.

Example 1

5 g of the bleached unbeaten softwood pulp (manufactured by Nippon Paper Industries, Co., Ltd.) (bone dry mass) was added to 500 mL of aqueous solution in which 78 mg (0.5 mmol) of TEMPO (manufactured by Sigma-Aldrich Corp.) and 754 mg (7.4 mmol) of sodium bromide were dissolved. The resulting mixture was stirred until the pulp was uniformly dispersed. After 14 mL of aqueous 2 M sodium hypochlorite solution was added to the reaction system, the pH value thereof was adjusted to 10.3 with aqueous 0.5 N hydrochloric acid solution to start the oxidation reaction. Since the pH value in the system lowered during the reaction, aqueous 0.5 N sodium hydroxide solution was added as appropriate to keep the pH value at 10. After 2 hours of the reaction, the reaction mixture was filtrated with a glass filter, and the filtered material was sufficiently washed with water to obtain the oxidized cellulose having the amount of the carboxy group of 1.60 mmol/g.

Next, the obtained oxidized cellulose slurry was adjusted to 1% (w/v) by adding water, and then treated with an ultrahigh pressure homogenizer (20° C., 140 MPa) for 3 times to obtain transparent gel-like dispersion liquid of the carboxylated cellulose nanofiber salt (1% (w/v)).

The cation exchange resins ("Amberjet 1024", manufactured by Organo Corp.) were added to the dispersion liquid of the obtained carboxylated cellulose nanofiber salt, and then stirred at 20° C. for 0.3 hour to bring them into contact with each other. Thereafter, the cation exchange resins and the water dispersion were separated through a metal mesh (sieve opening of 100 mesh) to obtain the acid type carboxylated cellulose nanofiber (nanofiber A).

The viscosity of the water dispersion of 1.00% by mass of the obtained acid type carboxylated cellulose nanofiber was 925 Pa·s under the shear velocity condition (0.00417 $s^{-1}$ at 30° C.) and 920 Pa·s under the condition (0.00671 $s^{-1}$ at 30° C.). The results are shown in Table 1.

In the obtained acid type carboxylated cellulose nanofiber, the average fiber length was 549 nm, the average fiber diameter was 2.83 nm, the ratio of fibers having the fiber length of 300 nm or shorter was 29.3%, and the ratio of fibers having the fiber length of 600 nm or longer was 23.2%. The results are shown in Table 2, and the ratio of the fiber length distribution is illustrated in FIG. 1.

Comparative Example 1

The carboxylated cellulose nanofiber was obtained following the same procedure as Example 1 except that the desalting process was changed as follows.

10% aqueous hydrochloric acid solution was added to the dispersion liquid of the carboxylated cellulose nanofiber salt until the pH value reached 2.4, and then stirred at 20° C. for 0.4 hour to bring them into contact with each other. Thereafter, the washing and dehydration treatment was repeated for 3 times, and then followed by filtration. Water was added to the filtered material to adjust the concentration thereof to 1.0% (w/v), and then the resultant was treated with an ultrahigh pressure homogenizer (20° C., 140 MPa) twice to obtain transparent gel-like dispersion liquid of the H-type carboxylated cellulose nanofiber (1% (w/v)).

The viscosity of the water dispersion of 1.00% by mass of the obtained carboxylated cellulose nanofiber was 336 Pa·s under the shear velocity condition (0.00417 $s^{-1}$ at 30° C.) and 350 Pa·s under the condition (0.00671 $s^{-1}$ at 30° C.) The results are shown in Table 1.

The average fiber length of the obtained carboxylated cellulose nanofiber was 503 nm and the average fiber diameter thereof was 2.55 nm.

Example 2

5 g of the bleached unbeaten softwood pulp (manufactured by Nippon Paper Industries, Co., Ltd.) (bone dry mass) was added to 500 mL of aqueous solution in which 78 mg (0.5 mmol) of TEMPO (manufactured by Sigma-Aldrich Corp.) and 754 mg (7.4 mmol) of sodium bromide were dissolved. The resulting mixture was stirred until the pulp was uniformly dispersed. After 11 mL of aqueous 2 M sodium hypochlorite solution was added to the reaction system, the pH value thereof was adjusted to 10.3 with aqueous 0.5 N hydrochloric acid solution to start the oxidation reaction. Since the pH value in the system lowered during the reaction, aqueous 0.5 N sodium hydroxide solution was added as appropriate to keep the pH value at 10. After 1.5 hours of the reaction, the reaction mixture was filtrated with a glass filter, and the filtered material was sufficiently washed with water to obtain the oxidized cellulose having the amount of the carboxy group of 1.23 mmol/g.

Next, the obtained oxidized cellulose slurry was adjusted to 1% (w/v) by adding water, and then treated with an ultrahigh pressure homogenizer (20° C., 140 MPa) twice to obtain transparent gel-like dispersion liquid of the carboxylated cellulose nanofiber salt (1% (w/v)).

The cation exchange resins ("Amberjet 1024", manufactured by Organo Corp.) were added to the dispersion of the obtained carboxylated cellulose nanofiber salt, and then stirred at 20° C. for 0.3 hour to bring them into contact with each other. Thereafter, the cation exchange resins and the water dispersion were separated through a metal mesh (sieve opening of 100 mesh) to obtain the acid type carboxylated cellulose nanofiber (nanofiber).

The viscosity of the water dispersion of 1.00% by mass of the obtained acid type carboxylated cellulose nanofiber was 18,300 Pa·s under the shear velocity condition (0.00417 $s^{-1}$ at 30° C.) and 17,800 Pa·s under the condition (0.00671 $s^{-1}$ at 30° C.). The results are shown in Table 1.

The average fiber length of the obtained acid type carboxylated cellulose nanofiber was 624 nm, and the average fiber diameter thereof was 3.11 nm.

Example 3

5 g of the bleached unbeaten softwood pulp (manufactured by Nippon Paper Industries, Co., Ltd.) (bone dry mass) was added to 500 mL of aqueous solution in which 78 mg (0.5 mmol) of TEMPO (manufactured by Sigma-Aldrich Corp.) and 754 mg (7.4 mmol) of sodium bromide were dissolved. The resulting mixture was stirred until the pulp was uniformly dispersed. After 12 mL of aqueous 2 M sodium hypochlorite solution was added to the reaction system, the pH value thereof was adjusted to 10.3 with aqueous 0.5 N hydrochloric acid solution to start the oxidation reaction. Since the pH value in the system lowered during the reaction, aqueous 0.5 N sodium hydroxide solution was added as appropriate to keep the pH value at 10. After 2 hours of the reaction, the reaction mixture was filtrated with a glass filter, and the filtered material was sufficiently washed with water to obtain the oxidized cellulose having the amount of the carboxy group of 1.50 mmol/g.

Next, the obtained oxidized cellulose slurry was adjusted to 1% (w/v) by adding water, and then treated with an ultrahigh pressure homogenizer (20° C., 140 MPa) for 3 times to obtain transparent gel-like dispersion liquid of the carboxylated cellulose nanofiber salt (1% (w/v)).

The cation exchange resins ("Amberjet 1024", manufactured by Organo Corp.) were added to the dispersion liquid of the obtained carboxylated cellulose nanofiber salt, and then stirred at 20° C. for 0.3 hour to bring them into contact with each other. Thereafter, the cation exchange resins and the water dispersion were separated through a metal mesh (sieve opening of 100 mesh) to obtain the acid type carboxylated cellulose nanofiber (nanofiber).

The viscosity of the water dispersion of 1.00% by mass of the obtained acid type carboxylated cellulose nanofiber was 995 Pa·s under the shear velocity condition (0.00417 $s^{-1}$ at 30° C.) and 970 Pa·s under the condition (0.00671 $s^{-1}$ at 30° C.). The results are shown in Table 1.

The average fiber length of the obtained acid type carboxylated cellulose nanofiber was 570 nm, and the average fiber diameter thereof was 2.85 nm.

Example 4

5 g of the bleached unbeaten softwood pulp (manufactured by Nippon Paper Industries, Co., Ltd.) (bone dry mass) was added to 500 mL of aqueous solution in which 78 mg (0.5 mmol) of TEMPO (manufactured by Sigma-Aldrich Corp.) and 754 mg (7.4 mmol) of sodium bromide were dissolved. The resulting mixture was stirred until the pulp was uniformly dispersed. After 6 mL of aqueous 2 M sodium hypochlorite solution was added to the reaction system, the pH value thereof was adjusted to 10.3 with aqueous 0.5 N hydrochloric acid solution to start the oxidation reaction. Since the pH value in the system lowered during the reaction, aqueous 0.5 N sodium hydroxide solution was added as appropriate to keep the pH value at 10. After 0.5 hour of the reaction, the reaction mixture was filtrated with a glass filter, and the filtered material was sufficiently washed with water to obtain the oxidized cellulose having the amount of the carboxy group of 0.60 mmol/g.

Next, the obtained oxidized cellulose slurry was adjusted to 1% (w/v) by adding water, and then treated with an ultrahigh pressure homogenizer (20° C., 140 MPa) twice to obtain transparent gel-like dispersion liquid of the carboxylated cellulose nanofiber salt (1% (w/v)).

The cation exchange resins ("Amberjet 1024", manufactured by Organo Corp.) was added to the dispersion liquid of the obtained carboxylated cellulose nanofiber salt, and then stirred at 20° C. for 0.3 hour to bring them into contact with each other. Thereafter, the cation exchange resins and the water dispersion were separated through a metal mesh (sieve opening of 100 mesh) to obtain the acid type carboxylated cellulose nanofiber (nanofiber).

The viscosity of the water dispersion of 1.00% by mass of the obtained acid type carboxylated cellulose nanofiber was 24,100 Pa·s under the shear velocity condition (0.00417 $s^{-1}$ at 30° C.) and 23,300 Pa·s under the condition (0.00671 $s^{-1}$ at 30° C.). The results are shown in Table 1.

The average fiber length of the obtained acid type carboxylated cellulose nanofiber was 840 nm, and the average fiber diameter thereof was 3.22 nm.

TABLE 1

|  | Amount of carboxy group (mmol/g) | Average fiber length (nm) | Shear velocity ($s^{-1}$) | Viscosity (Pa · s) |
|---|---|---|---|---|
| Example 1 | 1.60 | 549 | 0.00417 | 925 |
|  |  |  | 0.00671 | 920 |
| Comparative Example 1 | 1.60 | 503 | 0.00417 | 336 |
|  |  |  | 0.00671 | 350 |
| Example 2 | 1.23 | 624 | 0.00417 | 18300 |
|  |  |  | 0.00671 | 17800 |
| Example 3 | 1.50 | 570 | 0.00417 | 995 |
|  |  |  | 0.00671 | 970 |
| Example 4 | 0.60 | 840 | 0.00417 | 24100 |
|  |  |  | 0.00671 | 23300 |

As can be seen in Table 1, in the acid type carboxylated cellulose nanofiber prepared by the desalting treatment with the cation exchange resins, when the amount of the carboxy group was 1.60 mmol/g, the viscosity thereof was 925 Pa·s or 920 Pa·s in the low shear region of 0.00417 or 0.00671 s$^{-1}$, respectively (see Example 1), and when the amount of the carboxy group was 1.50 mmol/g, the viscosity thereof was 995 Pa·s or 970 Pa·s (see Example 3). When the amount of the carboxy group was 1.23 mmol/g, the viscosity thereof was 18,300 Pa·s or 17,800 Pa·s (see Example 2), and when the amount of the carboxy group was 0.60 mmol/g, the viscosity thereof was 24,100 Pa·s or 23,300 Pa·s (see Example 4), which were high viscosity.

On the other hand, in the acid type carboxylated cellulose nanofiber prepared by the desalting treatment with hydrochloric acid, when the amount of the carboxy group was 1.60 mmol/g, which was the same as Example 1, the viscosity thereof was 336 Pa·s or 350 Pa·s in the low shear region of 0.00417 s$^{-1}$ or 0.00671 s$^{-1}$, respectively (see Comparative Example 1), which were low viscosity. From this, it was found that depending on the process in the desalting treatment, physical properties of the obtained acid type carboxylated cellulose nanofiber, in particular, the viscosity in the low shear region was different. Accordingly, in the acid type carboxylated cellulose nanofiber, a wide range of application can be expected by changing the process of the desalting treatment in accordance with the use thereof.

Example 5

5 g of the bleached unbeaten softwood pulp (manufactured by Nippon Paper Industries, Co., Ltd.) (bone dry mass) was added to 500 mL of aqueous solution in which 78 mg (0.5 mmol) of TEMPO (manufactured by Sigma-Aldrich Corp.) and 754 mg (7.4 mmol) of sodium bromide were dissolved. The resulting mixture was stirred until the pulp was uniformly dispersed. After 16 mL of aqueous 2 M sodium hypochlorite solution was added to the reaction system, the pH value thereof was adjusted to 10.3 with aqueous 0.5 N hydrochloric acid solution to start the oxidation reaction. Since the pH value in the system lowered during the reaction, aqueous 0.5 N sodium hydroxide solution was added as appropriate to keep the pH value at 10. After 2 hours of the reaction, the reaction mixture was filtrated with a glass filter, and the filtered material was sufficiently washed with water to obtain the oxidized cellulose having the amount of the carboxy group of 1.60 mmol/g.

Next, to the 5% (w/v) slurry of the oxidized cellulose, hydrogen peroxide was added with the amount of 1% (w/v) relative to the oxidized cellulose, and the pH of the resulting mixture was adjusted to 12 with 1 M sodium hydroxide. This slurry was subjected to the hydrolysis treatment at 80° C. for 2 hours. Thereafter, the treated slurry was filtrated by a glass filter and sufficiently washed with water.

The 2% (w/v) hydrolyzed oxidized cellulose slurry was treated with an ultrahigh pressure homogenizer (20° C., 140 MPa) for 5 times to obtain transparent gel-like dispersion liquid of the carboxylated cellulose nanofiber salt (1% (w/v)).

A cation exchange resins ("Amberjet 1024", manufactured by Organo Corp.) were added to the dispersion liquid of the obtained carboxylated cellulose nanofiber salt, and then stirred at 20° C. for 0.3 hour to bring them into contact with each other. Thereafter, the cation exchange resins and the water dispersion were separated through a metal mesh (sieve opening of 100 mesh) to obtain the acid type carboxylated cellulose nanofiber (nanofiber B) in a high yield of 92%.

In the obtained acid type carboxylated cellulose nanofiber, the average fiber length was 311 nm, the average fiber diameter was 5.73 nm, the ratio of fibers having the fiber length of 300 nm or shorter was 79.9%, and the ratio of fibers having the fiber length of 600 nm or longer was 1.1%. The results are shown in Table 2, and the ratio of the fiber length distribution is illustrated in FIG. 1.

TABLE 2

|  | Example 1 | Example 5 |
| --- | --- | --- |
| Amount of carboxy group (mmol/g) | 1.60 | 1.60 |
| Average fiber length (nm) | 549 | 311 |
| Average fiber diameter (nm) | 2.83 | 5.73 |
| Ratio of fibers having fiber length of 300 nm or shorter (%) | 29.3 | 79.9 |
| Ratio of fibers having fiber length of 600 nm or longer (%) | 23.2 | 1.1 |

As can be seen in Table 2, in the carboxylated cellulose nanofiber obtained by the hydrolysis treatment, the average fiber length was short, and the ratios of the fibers having the fiber length of 300 nm or shorter was high, and the ratio of the fibers having the fiber length of 600 nm or longer were very low (see Examples 1 and 5). Therefore, the fibers are converged to the region of the short fiber length. Accordingly, it can be expected to be applied to the field where the cellulose nanofiber having a short fiber length is desired.

The invention claimed is:

1. An acid type carboxylated cellulose nanofiber, comprising a carboxy group at least in part of a constituent unit constituting a cellulose molecular chain,
    wherein a viscosity of water dispersion with a content of 1.00% by mass is 400 Pa·s or higher at a shear velocity of 0.00417 s$^{-1}$ or 0.000671 s$^{-1}$ at 30° C.

2. The acid type carboxylated cellulose nanofiber according to claim 1, wherein at least part of the cellulose molecular chain is composed of a constituent unit having a carboxy group formed by selectively oxidizing a carbon atom having a primary hydroxy group at a C6 position of a glucopyranose unit.

3. The acid type carboxylated cellulose nanofiber according to claim 1,
    wherein an amount of the carboxy group relative to a bone dry mass of the carboxylated cellulose nanotiber is from 0.6 to 2.0 mmol/g.

4. The acid type carboxylated cellulose nanofi er according to claim
    wherein an amount of the carboxy group relative to a bone dry mass of the carboxylated cellulose nanofiber is from 0.8 to 2.0 mmol/g.

5. An acid type carboxylated cellulose nanofiber, comprising a carboxy group at least in part of a constituent unit constituting a cellulose molecular chain,
    wherein an average fiber length is from 50 to 500 nm, and a ratio of fibers having a fiber length of 300 nm or shorter is 50% or higher, and a ratio of fibers having a fiber length of 600 nm of longer is lower than 20%.

6. The acid type carboxylated cellulose nanofiber according to claim 5, wherein an average fiber diameter is from 2 to 50 nm.

7. The acid type carboxylated cellulose nanofiber according to claim 5, wherein an average fiber diameter is from 2 to 30 nm.

* * * * *